United States Patent
Jang

(10) Patent No.: US 12,089,764 B2
(45) Date of Patent: Sep. 17, 2024

(54) MOTION PILLOW

(71) Applicant: TENMINDS CO., LTD., Seoul (KR)

(72) Inventor: Seung Woong Jang, Seoul (KR)

(73) Assignee: TENMINDS CO., LTD., Seoul (KR)

( * ) Notice: Subject to any disclaimer, the term of this patent is extended or adjusted under 35 U.S.C. 154(b) by 359 days.

(21) Appl. No.: 17/606,906

(22) PCT Filed: Jan. 31, 2021

(86) PCT No.: PCT/KR2021/000489
§ 371 (c)(1),
(2) Date: Oct. 27, 2021

(87) PCT Pub. No.: WO2021/201391
PCT Pub. Date: Oct. 7, 2021

(65) Prior Publication Data
US 2022/0202213 A1 Jun. 30, 2022

(30) Foreign Application Priority Data

Mar. 31, 2020 (KR) .................. 10-2020-0038918

(51) Int. Cl.
*A47G 9/10* (2006.01)
*A47G 9/00* (2006.01)

(52) U.S. Cl.
CPC .......... *A47G 9/1027* (2013.01); *A47G 9/1045* (2013.01); *A47G 2009/003* (2013.01)

(58) Field of Classification Search
CPC ............ A47G 9/1027; A47G 9/1045; A47G 2009/003; A47G 9/10; A47G 9/1081;
(Continued)

(56) References Cited

U.S. PATENT DOCUMENTS

| | | | |
|---|---|---|---|
| 11,424,646 B2 * | 8/2022 | Holmvik | A47C 27/083 |
| 2012/0079660 A1 | 4/2012 | Chen | |
| 2016/0066716 A1 * | 3/2016 | Rao | A61B 5/6814 |
| | | | 600/26 |

FOREIGN PATENT DOCUMENTS

| CN | 104172825 A | 12/2014 |
|---|---|---|
| CN | 106235825 A | 12/2016 |

(Continued)

OTHER PUBLICATIONS

European Search Report For EP 21780598.5 issued on Jun. 15, 2023 from European patent office in a counterpart European patent application.

(Continued)

*Primary Examiner* — David R Hare
*Assistant Examiner* — Madison Emanski
(74) *Attorney, Agent, or Firm* — The PL Law Group, PLLC

(57) ABSTRACT

A motion pillow according to an embodiment of the present disclosure includes a body, a motion system, a connector, and a valve. The body includes a plurality of airbags provided therein. The motion system includes a pump allowing air to enter and exit the airbags, a sensor measuring air pressures of the airbags, a sound receiver receiving sound from around the body, and a controller controlling operating mode in accordance with measurements of the sensor. The connector connects the airbags and the motion system. The valve opens and closes the connector. When at least one airbag among the plurality of airbags is pressed and air is introduced to the sensor through the connector, the controller is configured to switch the operating mode from standby mode to active mode. Significantly improved convenience and satisfaction of sleep are provided to users.

8 Claims, 5 Drawing Sheets

(58) Field of Classification Search
CPC .......... A47G 2200/143; A47G 9/1036; A47G 2009/1018; A47G 9/109; A47G 2009/006; A61M 2205/07; A61M 2205/3331; A61M 2230/63; A61M 21/02; A61M 2021/0022; A61B 5/4806; A61B 5/4818; A61B 5/4815; A61F 5/56; A47C 27/083
USPC ....................................................... 5/644, 13
See application file for complete search history.

(56) References Cited

FOREIGN PATENT DOCUMENTS

| | | | | |
|---|---|---|---|---|
| CN | 106293010 A | | 1/2017 | |
| CN | 107811746 A | | 3/2018 | |
| CN | 108969175 A | | 12/2018 | |
| JP | 3064571 U | | 1/2000 | |
| JP | 3071127 U | | 8/2000 | |
| JP | 2006020722 A | * | 1/2006 | ............ A61F 5/56 |
| JP | 2006-304814 A | | 11/2006 | |
| JP | 2011-045400 A | | 3/2011 | |
| JP | 2019051070 A | * | 4/2019 | ............ A47G 9/10 |
| KR | 10-0758780 B1 | | 9/2007 | |
| KR | 10-2008-0075263 A | | 8/2008 | |
| KR | 10-2018-0130928 A | | 12/2018 | |
| KR | 10-1959030 B1 | | 3/2019 | |
| KR | 10-2023362 B1 | | 11/2019 | |
| KR | 10-2065513 B1 | | 1/2020 | |
| KR | 10-2073296 B1 | | 2/2020 | |
| KR | 10-2182080 B1 | | 11/2020 | |
| WO | WO 2016/192122 A1 | | 12/2016 | |
| WO | WO 2019/107657 A1 | | 6/2019 | |

OTHER PUBLICATIONS

Office action issued on May 9, 2023 from Japan Intellectual Property Office in a counterpart Japanese Patent Application No. 2021-0562171 (English translation is also submitted herewith.).

International Search Report for PCT/KR2021/000489 mailed on May 10, 2021.

Office action issued on Jul. 25, 2022 from China Patent Office in a counterpart China Patent Application No. 202180003115.4 (all the cited references are listed in this IDS.) (English translation is also submitted herewith.).

Office action issued on Nov. 8, 2022 from Japan Intellectual Property Office in a counterpart Japanese Patent Application No. 2021-562171 (all the cited references are listed in this IDS.) (English translation is also submitted herewith.).

* cited by examiner

MOTION PILLOW

CROSS REFERENCE TO RELATED APPLICATIONS AND CLAIM OF PRIORITY

This application claims benefit under 35 U.S.C. 119(e), 120, 121, or 365(c), and is a National Stage entry from International Application No. PCT/KR2021/000489, filed Jan. 13, 2021, which claims priority to the benefit of Korean Patent Application No. 10-2020-0038918 filed in the Korean Intellectual Property Office on Mar. 31, 2020, the entire contents of which are incorporated herein by reference.

BACKGROUND

1. Technical Field

The present disclosure relates to a motion pillow and, more particularly, to a motion pillow able to change the motion thereof.

2. Background Art

Recently, along with increasing attention to the Internet of things (IoT) in which sensors are attached to objects referred to as things in order to enable real-time data exchange, a smart pillow, a smart pad, and the like, configured to alleviate sleep disorders of users and assist in providing sound sleep to users, have been proposed.

Reflecting this trend, Korean Patent Application Publication No. 10-2008-0075263 discloses a pillow height adjustment device using an air cell. The pillow height adjustment device is configured to adjust the air pressure of an air cell disposed inside a pillow using a body pressure sensor attached to the external surface of the pillow, thereby adjusting the height of the pillow to be suitable to the shape of the head, the shape of the neck portion, or the like of a user. In addition, Korean Patent No. 10-0758780 discloses a speaker disposed inside a pillow to provide improved convenience to a user.

However, a separate device mounted externally on or internally in a pillow may cause a user to feel inconvenience. This may create an adverse effect on sleep, contrary to the intended effect of the device. In order to alleviate sleep disorders of users, the ability to accurately determine the position of a user while adjusting the height of the pillow is required. However, none of the above-mentioned related-art solutions has met this requirement.

In addition, since electric components are disposed on a pillow for position detection, there may be problems in that the possibility of malfunctioning or damage is increased and the body of the user is directly exposed to electromagnetic radiation.

SUMMARY

Accordingly, the present disclosure has been made in consideration of the above-described problems occurring in the related art, and the present disclosure is intended to provide a motion pillow able to provide more ideal sleep to a user by controlling the movement thereof and to be used more conveniently.

According to an embodiment of the present disclosure, a motion pillow may include: a body including a plurality of airbags provided therein; a motion system including a pump allowing air to enter and exit the airbags, a sensor measuring air pressures of the airbags, a sound receiver receiving sound from around the body, and a controller controlling operating mode in accordance with measurements of the sensor; a connector connecting the airbags and the motion system; and a valve opening and closing the connector. When at least one airbag among the plurality of airbags is pressed and air is introduced to the sensor through the connector, the controller is configured to switch the operating mode from standby mode to active mode.

When the operating mode is switched to the active mode, the controller is configured to measure the air pressures of the airbags by operating the pump and, only when a first difference between a maximum air pressure and a minimum air pressure among the measured air pressures is higher than a threshold value, maintain the active mode.

The active mode may comprise: a start step of supplying power to the pump when introduction of air to the sensor is measured; a first measurement step of measuring the first difference value by injecting air into the airbags; and a re-switching step of re-switching the operating mode to the standby mode when the first difference value is equal to or lower than the threshold value.

The active mode may further comprise, after the first measurement step, an analysis step of analyzing a movement of a user by measuring the air pressures of the airbags at every predetermined first time when the first difference is higher than the threshold value.

In the analysis step may comprise, even when the first time has not passed, when the user is determined to be in an abnormal state as a result of analyzing the sound received by the sound receiver, measuring the air pressures of the airbags and inducing a movement of the user by injecting air into an airbag having the maximum air pressure among the airbags.

The motion system may further include a wireless charger connected to a power supply. The standby mode may include only maintaining the sensor and the wireless charger in operating states so as to measure a change in the air pressures of the airbags.

After the analysis step, when a second difference between a maximum air pressure and a minimum air pressure is lower than the threshold value in response to a significant decrease in the air pressure of at least one airbag among the airbags, the motion system is configured to switch the operating mode to the standby mode.

The standby mode may include: a standby-maintaining step of maintaining the active mode for the predetermined first time when the second difference is lower than the threshold value; a re-measurement step of re-measuring air pressures of the airbags, respectively, and measuring a third difference between a maximum air pressure and a minimum air pressure among the re-measured air pressures; and a standby-start step of stopping supply of power to the motion pillow except for the sensor and the wireless charger only when the third difference is lower than the threshold value.

The motion system is further configured to maintain air injected into each of the airbags in the re-measurement step and, when a rapid increase in the air pressure of at least one airbag of the airbags occurs in the standby mode, re-switch the operating mode to the active mode to circulate air.

As set forth above, a variety of effects including the following effects may be expected from the technical solution of the present disclosure as described above. It should be understood, however, that all of the following effects are not necessarily required in the present disclosure.

The motion pillow according to the present disclosure switches the operating mode from the standby mode to the active mode and from the active mode to the standby mode in response to a change in the air pressure of the airbags so as to operate without being separately manipulated by a user, thereby providing improved convenience to the user.

In addition, even when there is a change in the air pressure of the airbags, the motion pillow primarily sets the threshold value and secondarily provides the standby-maintaining step to prevent an unnecessary operation or a malfunction in which the operating mode is accidentally switched to the standby mode, thereby maximizing improved convenience and improving satisfaction of the user.

In addition, when the sound receiver detects an abnormal state of the user, the movement of the user is induced, thereby improving the quality of sleep of the user. An additional function, such as the wireless charger, is further provided to improve satisfaction of the user.

Here, an electric component, such as the sound receiver or the wireless charger, is provided separately from the body in order to minimize a sleep disturbance factor, thereby improving the quality of sleep of the user and minimizing the possibility of damage.

DETAILED DESCRIPTION

Hereinafter, specific embodiments of the present disclosure will be described in detail. Detailed descriptions of known functions and components will be omitted in the case in which the subject matter of the present disclosure may be rendered unclear.

Figure 1:
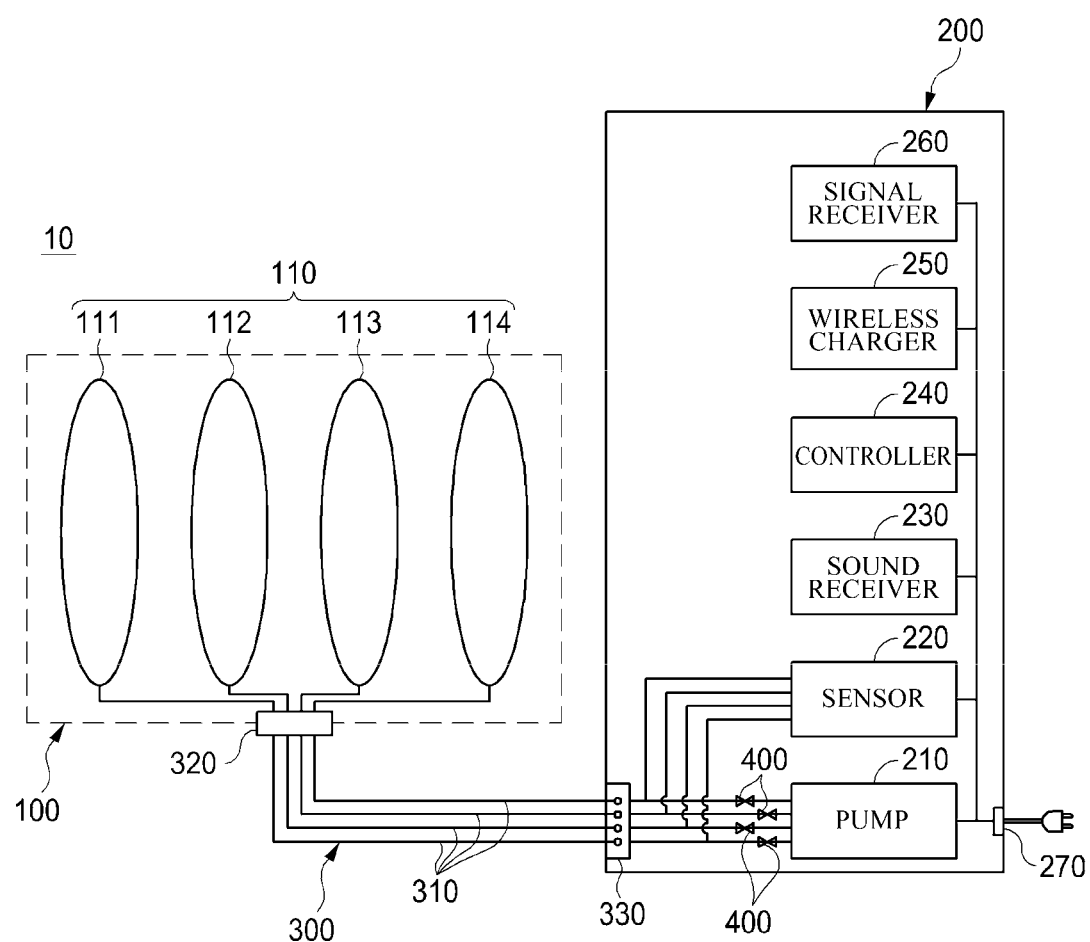
FIG. 1 is a schematic diagram illustrating a motion pillow according to an embodiment of the present disclosure.
Figure 2:
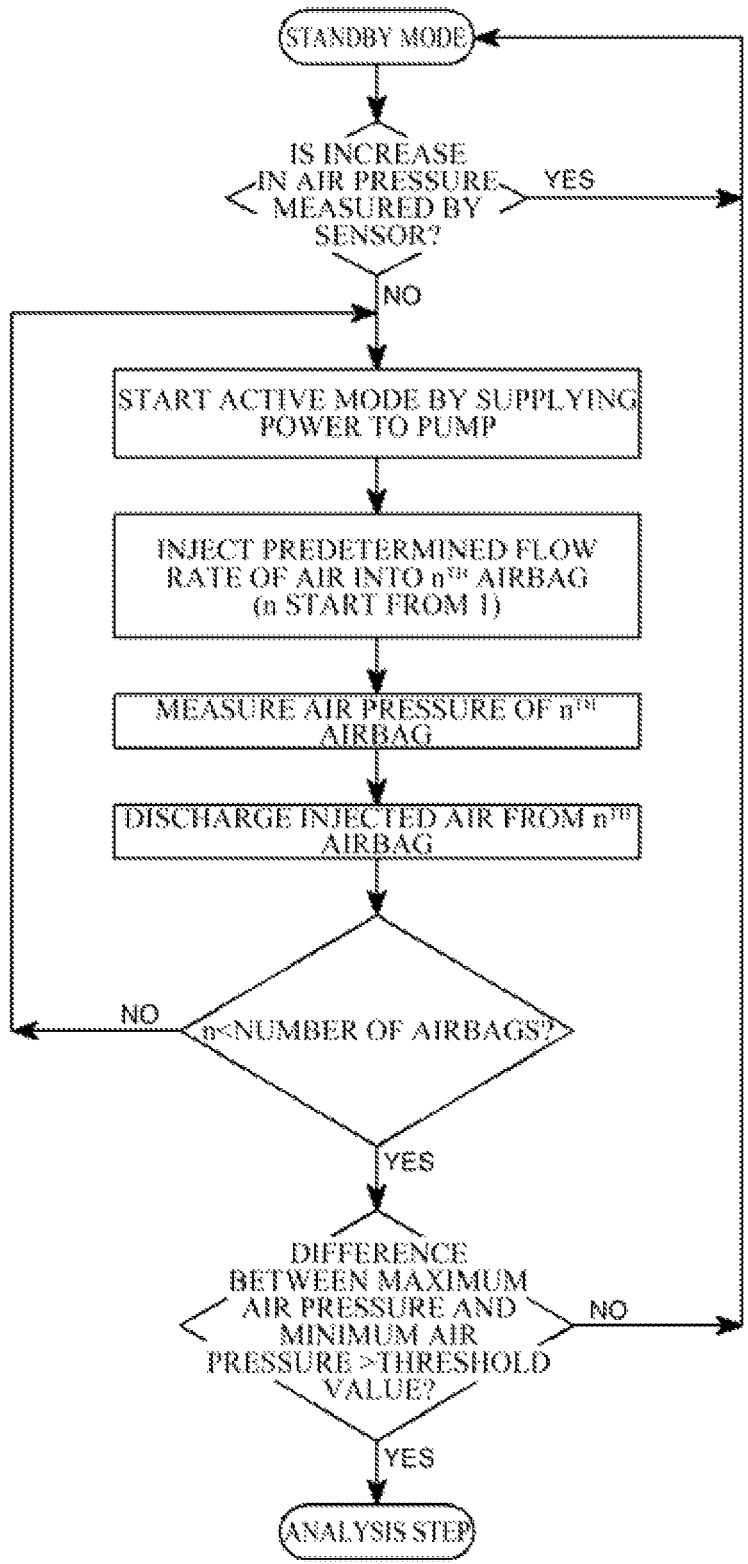
FIG. 2 is a flowchart illustrating a process of switching the motion pillow according to the present disclosure from standby mode to active mode.
Figure 3:
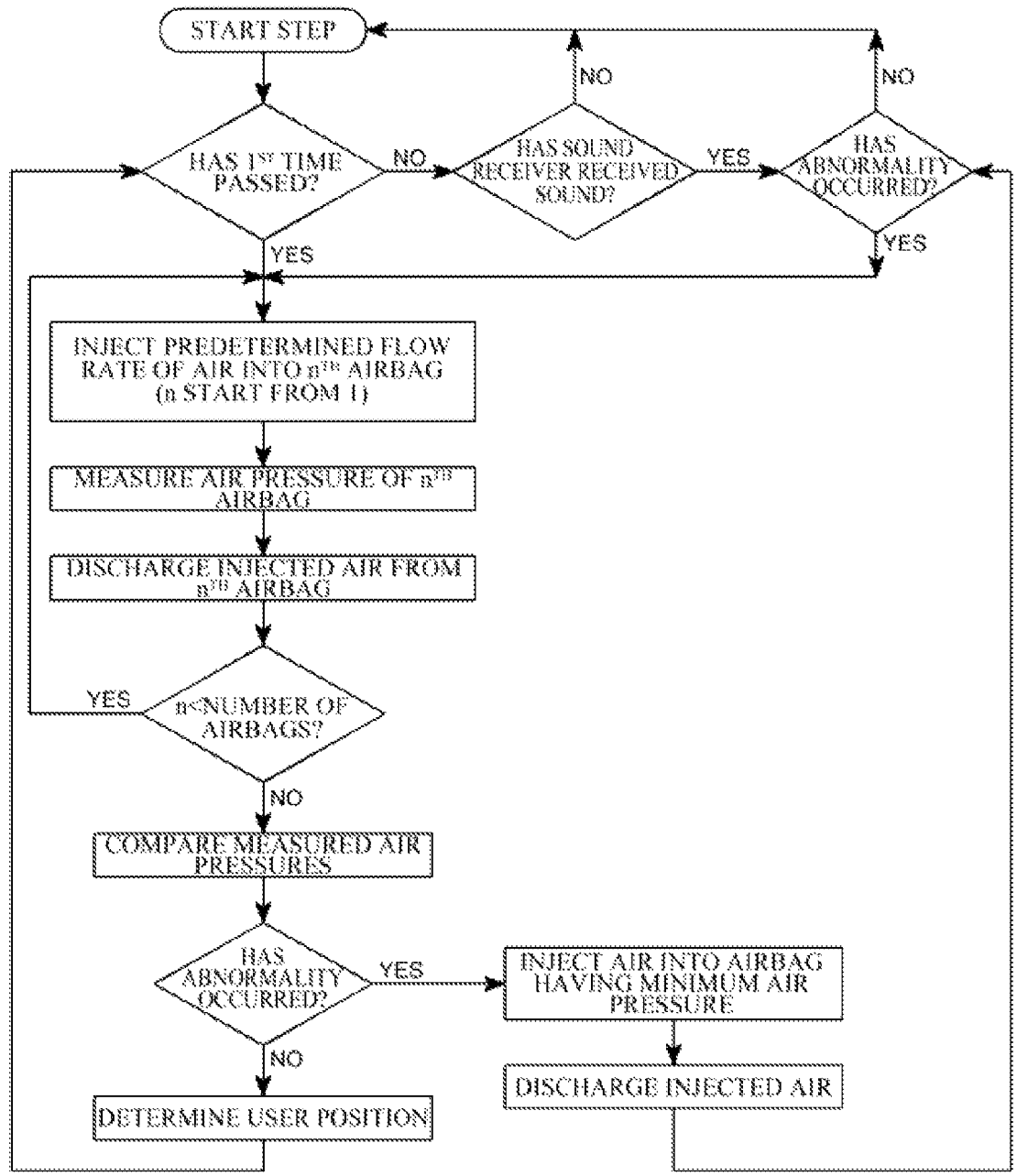
FIG. 3 is a flowchart illustrating a process of the analysis step in the active mode of FIG. 2.
Figure 4:
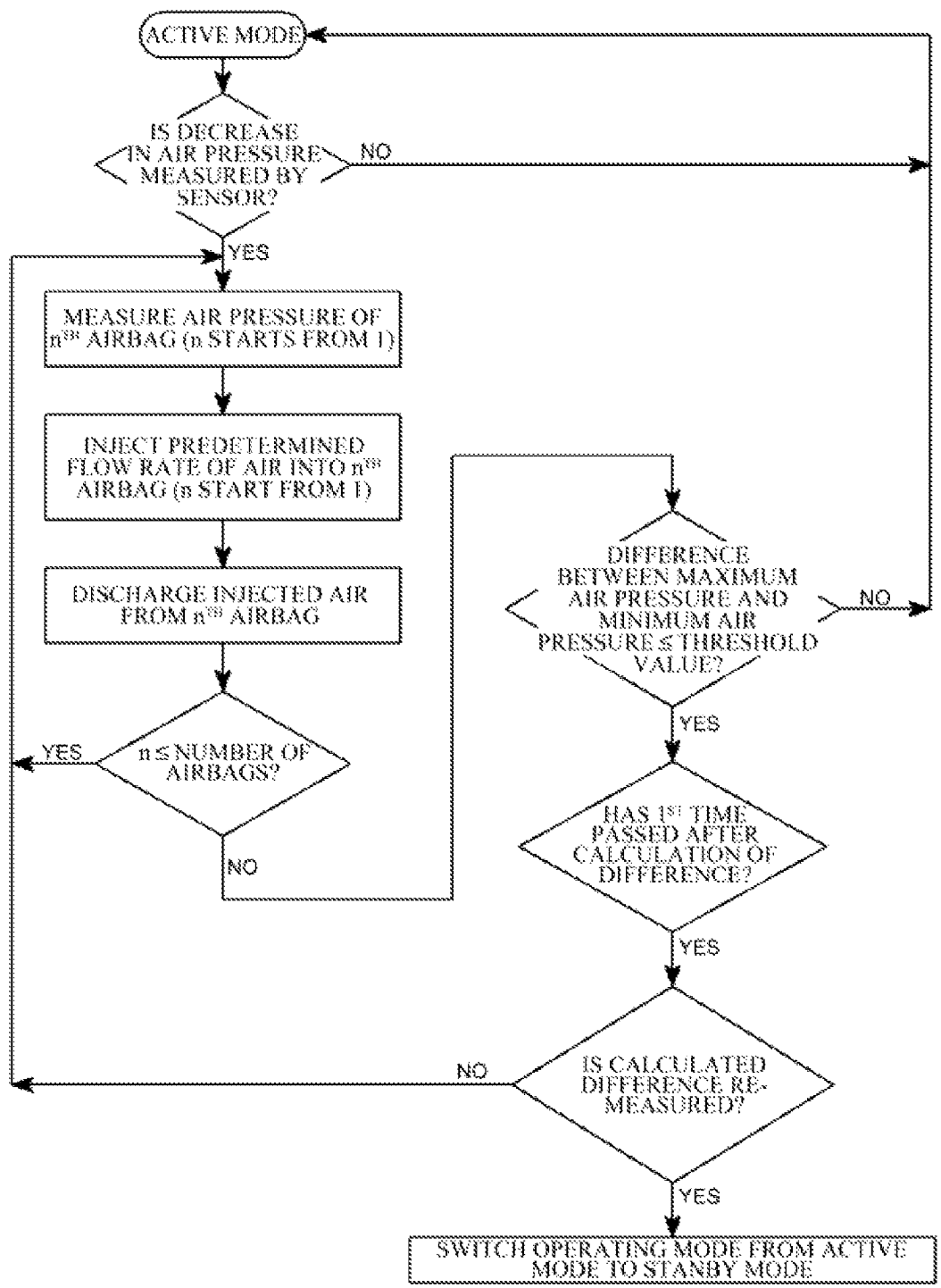
FIG. 4 is a flowchart illustrating a process of switching the motion pillow according to the present disclosure from the active mode to the standby mode.
Figure 5:
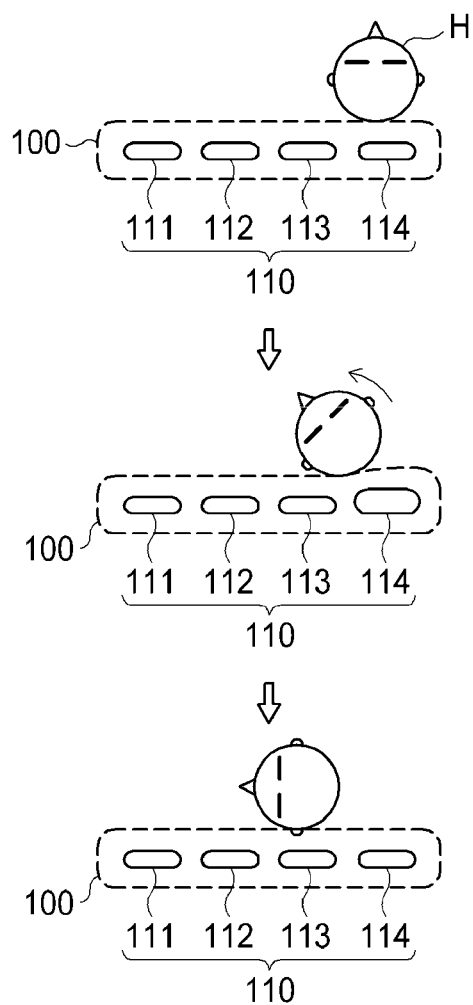
FIG. 5 is a diagram illustrating a process of inducing the movement of a user.

FIG. 1 is a schematic diagram illustrating a motion pillow according to an embodiment of the present disclosure, FIG. 2 is a flowchart illustrating a process of switching the motion pillow according to the present disclosure from standby mode to active mode, FIG. 3 is a flowchart illustrating a process of the analysis step in the active mode of FIG. 2, FIG. 4 is a flowchart illustrating a process of switching the motion pillow according to the present disclosure from the active mode to the standby mode, and FIG. 5 is a diagram illustrating a process of inducing the movement of a user.

Referring to FIGS. 1 to 5, a motion pillow 10 according to an embodiment of the present disclosure includes a body 100, a motion system 200, a connector 300, and valves 400. The body 100 has a plurality of airbags 110 disposed therein. The motion system 200 includes a pump 210 allowing air to enter and exit the airbags 110, a sensor 220 measuring air pressures of the airbags 110, a sound receiver 230 receiving sound from around the body 100, and a controller 240 controlling operating mode in accordance with measurements of the sensor 220. The connector 300 connects the airbags 110 and the motion system 200. The valves 400 open and close the connector 300. When at least one airbag 110 among the plurality of airbags 110 is pressed and air is introduced to the sensor 220 through the connector 300, the motion system 200 switches the operating mode from standby mode to active mode.

The motion pillow 10 includes the motion system 200 varying the motion of the body 100 by allowing air to enter and exit the airbags 110. The motion pillow 10 improves sleep disorders, such as snoring, which may occur during sleeping, thereby improving the quality of sleep.

Here, the motion pillow 10 according to the present disclosure automatically selects whether or not to operate depending on a change in the pressure of the airbags 110 without being manipulated by a user, thereby providing improved convenience to the user while improving satisfaction.

The body 100 has the plurality of airbags 110 disposed therein and is configured to allow air to enter or exit the airbags 110, thereby enabling the pillow to make a motion. In this manner, while the user is sleeping, the movement of the user is recorded or induced to alleviate sleep disorders, such as snoring.

The plurality of airbags 110 may be provided inside the body 100 to be spaced apart from each other at predetermined distances while being formed to have the same characteristics. However, the scope of the present disclosure is not limited thereto, and the airbags may have different sizes, materials, shapes, or the like depending on the design.

According to an embodiment of the motion pillow 10, the four airbags, i.e., a first airbag 111, a second airbag 112, a third airbag 113, and a fourth airbag 114, having the same characteristics, such as size, shape, material, coefficient of expansion, and maximum air capacity, are disposed in parallel at the same distances. Thus, it is possible to advantageously control the airbags 110 by a simpler logic.

According to another embodiment of the motion pillow 10, characteristics, such as size, shape, material, coefficient of expansion, and maximum air capacity, are different. The motion pillow 10 is configured such that not only the movement of the head of the user but also the movement of other body portions, such as the neck, may be recorded. The motion pillow 10 may more precisely induce the movement of the user, thereby increasing the effect of improving sleep disorders.

In other words, the airbags 110 of the motion pillow 10 according to the present disclosure are designed variously to increase the freedom of choice of the user and to improve satisfaction of the user.

The motion system 200 includes a pump 210 allowing air to enter and exit the airbags 110, the sensor 220 measuring the air pressure of the airbags 110, the sound receiver 230 receiving sound, the controller 240 controlling the operating mode depending on a value measured by the sensor 220, and a wireless charger 250 providing a wireless charging function. Here, a power supply 270 supplying power to internal electric components of the motion system is provided on one side of the motion system.

The pump 210 is connected to each of the plurality of airbags 110 through the connector 300 to selectively allow air to enter or exit each of the airbags 110. Here, the sensor 220 is also connected to each of the plurality of airbags 110 to measure the air pressure of each of the airbags 110. In this manner, the movement of the user may be more accurately determined during sleep, and the operating mode may be switched without being manipulated by a user. Consequently, the effect of improving the convenience of the user may be maximized.

This will be described in detail hereinafter in the description of the operating mode.

The controller 240 controls the operation of the motion system. Specifically, the controller 240 determines whether or not to apply power to the pump 210, controls the flow rate (or amount) of air entering or exiting the airbags 110, determines the operating mode depending on the value measured by the sensor 220, and analyzes the sound received by the sound receiver 230, thereby determining the abnormality of the user.

The wireless charger 250 is connected to the power supply 270. Even when the motion pillow 10 is in the standby mode, power is applied to the wireless charger 250, such that the user may use the wireless charger 250 as a wireless charging device for other devices. Thus, the usability of the motion pillow 10, which is only used for sleeping, may be increased.

A signal receiver 260 is connected to a communication device of the user, a server, or a database through a network using a network interface to communicate therewith. The signal receiver 260 may transmit sleep habits and the like of the user to an external device, thereby allowing the user to more easily access data regarding his or her sleep habits.

Here, the network interface may be implemented using publicly-known communication modules, such as a wired/wireless communication module, a network card, and an infrared (IR) communication module, in order to support various communication methods. In addition, available communication technologies may include Wi-Fi, wideband code-division multiple access (WCDMA), high speed downlink packet access (HSDPA), high speed uplink packet access (HSUPA), high speed packet access (HSPA), worldwide interoperability for microwave access (WIMAX), mobile WiMAX, wireless broadband (WiBro), $3^{rd}$ generation partnership project (3GPP), 5G, IR communication, long-term evolution (LTE), LTE advanced (LTE-A), Bluetooth, near-field communication (NFC), ZigBee®, location area network (LAN), wireless LAN, wide area network (WAN), personal area network (PAN), and the like.

Thus, the user may communicate with communication devices, be provided with information regarding the operation history of the motion pillow 10 for analyzing the abnormality during sleep (e.g., snoring) and improving the abnormality through a dedicated application installed in communication devices, and test whether or not the motion pillow is malfunctioning by allowing air to enter or exit the airbags 110 using the dedicated application.

The power supply 270 is provided on one side of the motion pillow to integrally supply power to electric components required for the motion pillow 10 and to components each providing an additional function. In this manner, a product may be simplified, thereby improving the convenience of the user and the external appearance of the product.

Thus, in the motion pillow 10 according to the present disclosure, electric components for the operation thereof may be separately disposed in the motion system 200 instead of being disposed internally or externally of the body 100. In this manner, elements for interrupting the sleep of the user and malfunction may be minimized, thereby providing more improved convenience to the user.

The connector 300 includes a plurality of cables 310 connected to the plurality of airbags 110, respectively, a first connecting portion 320 formed on one end to be connected to the body 100, and a second connecting portion 330 formed on the other end to be connected to the motion system 200. The airbags 110 and the motion system 200 may be easily connected by only coupling the first and second connecting portions 320 and 330.

Here, the body 100 has a complementary coupling structure to be coupled to the first connecting portion 320, and the motion system 200 has a complementary coupling structure to be coupled to the second connecting portion 330. The first and second connecting portions 320 and 330 may have different shapes, such that the user may more easily connect the first and second connecting portions to the body and the motion system, respectively.

In addition, in the connector 300, the plurality of cables 310 may be covered and held by an integrated tube or an integrated holding means in order to prevent the cables 310 from being entangled and to improve the external appearance of the motion pillow 10.

The valves 400 are disposed on air passages connected to the plurality of cables 310 by the second connecting portion 330 so as to open and close the cables 310 through which air may enter or exit the airbags 110 as required. In the standby mode, the valves 400 are closed so that air discharged from the airbags 110 may be introduced to the sensor 220.

Here, the air passages are connected to the pump 210 such that air may selectively enter and exit each of the airbags 110, are branched between the second connecting portion 330 and the valves 400, and are connected to the sensor 220. In this manner, a rapid increase in the air pressure in the standby mode may be measured.

Thus, the motion pillow 10 according to the present disclosure may further include an electric component providing an additional function in addition to the functions of improving sleep disorders of the user and recording the sleep habits of the user. In addition to the sleeping time, the user may use the motion pillow. Consequently, the product usability of the motion pillow may be improved.

Hereinafter, the operating mode of the motion pillow 10 will be described in detail.

The operating mode of the motion pillow 10 is divided into the standby mode and the active mode. The standby mode is defined as a state in which the user does not use the motion pillow 10 although the motion system 200 is connected to a power source, such that power is applied to only some components. The active mode is defined as a state in which the user is using the motion pillow 10 and power is applied to all of the components.

In the standby mode, power is only applied to the wireless charger 250, the signal receiver 260, the sensor 220, and the controller 240, whereas the valves 400 are closed and are in standby for the motion pillow to be used by the user. When the user uses the motion pillow, at least one of the plurality of airbags 110 is pressed by the weight of the head. Then, air is introduced to the sensor 220 along the corresponding cable 310 and the corresponding air passage. Consequently, the pressure of air measured by the sensor 220 is rapidly increased and the motion system 200 responsively switches the operating mode from the standby mode to the active mode.

Specifically, in the motion system 200, when the instantaneous increase in the air pressure is measured by the sensor 220, power is supplied to the controller 240, which in turn operates the pump 210, thereby switching the operating mode from the standby mode to the active mode.

In other words, the process in which the operating mode is switched from the standby mode to the active mode includes: an operation start step of preparing for the motion of the body 100 by supplying power to the pump so that air may enter or exit the airbags 110 when an increase in the air pressure is measured by the sensor 220; a first measurement step of measuring the air pressure by injecting a predetermined amount of air into each of the airbags 110; a re-switching step of re-switching the operating mode to the standby mode when a first difference between the maximum air pressure and the minimum air pressure measured at the first measurement step is equal to or lower than a threshold value; and an analysis step of analyzing the movement of the user by measuring the air pressure of each of the airbags 110 at every predetermined first time when the first difference is higher than the threshold value.

Here, the threshold value is preset on the basis of the pressure difference between when the body 100 is pressed and when the body is not pressed. For example, only when the difference is in the range of from 4 psi to 8 psi, it is determined that the pillow is pressed by the head of the user to maintain the operating mode in the active mode. When the difference is out of this range, the operating mode is re-switched to the standby mode.

In addition, in the analysis step, the movement of the user during sleep is measured by periodically measuring the air pressure of each of the airbags 110 at every first time, and the sleep habits of the user are stored and recorded by transmitting information with regard to an external device.

Described in short, the motion pillow 10 according to the present disclosure may switch the operating mode from the standby mode to the active mode when the user simply lays the head on the motion pillow 10 without additionally manipulating and operating the motion pillow 10 in the standby mode. In this manner, it is possible to simplify the process of starting a typical wired electronic product, thereby providing improved convenience to the user.

In addition, even when the user accidentally falls asleep, the sleep habits may be recorded, so that the sleep habits may be continuously reviewed. The abnormality, such as sleep disorders, may be improved so as to improve the quality of sleep of the user, thereby significantly improving satisfaction of the user.

In addition, after the operating mode is switched to the active mode, when the first difference is equal to or lower than the threshold value, the operating mode may be re-switched to the standby mode in order to prevent any malfunction. Even in the standby mode, additional functions, such as a wireless charging function and a signal receiving function, may be performed, thereby maximizing the effect of improving convenience.

In the active mode in which the user is using the motion pillow 10 and power is being supplied to all of the components thereof, when the user raises the head, the weight applied to at least one of the plurality of airbags 110 is reduced, thereby significantly reducing the air pressure measured by the sensor 220. Consequently, the motion system 200 switches the operating mode from the active mode to the standby mode.

Specifically, when an instantaneous decrease in the air pressure is measured by the sensor 220, the motion system 200 may sequentially measure the air pressures of the airbags 110 and, only when a second difference between the maximum air pressure and the minimum air pressure among the measured air pressures is equal to or lower than a second threshold value, switches the operating mode.

Here, even when the second difference is equal to or lower than the second threshold value, after the predetermined first time has passed, the switching of the operating mode is performed by re-measuring the difference in order to prevent a malfunction.

In other words, the process of switching from the active mode to the standby mode includes: a standby-maintaining step of maintaining the active mode for the predetermined first time when a decrease in the air pressure is measured by the sensor 220 and the second difference between the maximum air pressure and the minimum air pressure among the air pressures measured from the airbags 110 is equal to or lower than the threshold value; a re-measurement step of measuring a third difference from the air pressures of the airbags 110 after the first time has passed; and a standby-start step of stopping the supply of power to the motion pillow except for the sensor 220 and the wireless charger 250 only when the third difference is equal to or lower than the threshold value.

However, since power is applied to the pump 210 in the process of switching from the active mode to the standby mode, the standby-maintaining step of measuring the second difference and the re-measurement step of measuring the third difference may measure the air pressures by injecting predetermined amounts of air into the airbags 110, respectively.

Thus, even when an instantaneous movement of the user occurs or the user wakes up briefly and falls asleep again, the motion pillow 10 according to the present disclosure can continuously record the sleep habits of the user, thereby improving satisfaction of the user.

In addition, although the first time set in each of the steps is 10 minutes in the motion pillow 10 according to an embodiment, the first time may be changed. The first time may be changed by the user by changing the setting as required.

The motion pillow 10 according to the present disclosure can automatically perform a set of procedures, such as sound reception, user status analysis, sequential air injection, air pressure measurement, and user movement recording, as designed in advance and repeatedly perform the set of procedures, thereby significantly improving the convenience of the user.

In addition, in the switching of the operating mode, switching conditions may be reviewed two times to minimize malfunctions. The motion system 200 may be separately provided on the body 100. Consequently, it is possible to minimize sleep disorders of the user and improve the external appearance of the product.

Although the exemplary embodiments of the present disclosure have been described for illustrative purposes, the scope of the present disclosure is not limited to the specific embodiments, and suitable modifications may be made without departing from the scope of the present disclosure defined by the Claims.

What is claimed is:

1. A motion pillow comprising:
   a body comprising a plurality of airbags provided therein;
   a motion system comprising a pump allowing air to enter and exit the airbags, a sensor measuring air pressures of the airbags, a sound receiver receiving sound from around the body, and a controller controlling an operating mode in accordance with measurements of the sensor;
   a connector connecting the airbags and the motion system; and
   a valve opening and closing the connector,
   wherein, when at least one airbag among the plurality of airbags is pressed and air is introduced to the sensor through the connector, the controller is configured to switch the operating mode from a standby mode, in which power is not supplied to the pump, to an active mode, in which power is supplied to the pump,
   wherein, when the operating mode is switched to the active mode, the controller is configured to measure the air pressures of the airbags by operating the pump, and wherein, when a user is determined to be in an abnormal state as a result of analyzing the sound received by the sound receiver, measuring the air pressures of the airbags and inducing a movement of the user by injecting air into an airbag, by maximizing the air pressure among the airbags.

2. The motion pillow according to claim 1, wherein, only when a first difference between a maximum air pressure and a minimum air pressure among the measured air pressures is higher than a threshold value, maintain the active mode.

3. The motion pillow according to claim 2, wherein the active mode comprises:
   a start step of supplying power to the pump when introduction of air to the sensor is measured;
   a first measurement step of measuring the first difference value by injecting air into the airbags; and
   a re-switching step of re-switching the operating mode to the standby mode when the first difference value is equal to or lower than the threshold value.

4. The motion pillow according to claim 3, wherein the active mode further comprises, after the first measurement step, an analysis step of analyzing the movement of the user by measuring the air pressures of the airbags at every predetermined first time when the first difference is higher than the threshold value.

5. ion pillow according to claim 4, wherein the motion system further comprises a wireless charger connected to a power supply; and
   the standby mode comprises only maintaining the sensor and the wireless charger in operating states so as to measure a change in the air pressures of the airbags.

6. The motion pillow according to claim 4, wherein, after the analysis step, when a second difference between the maximum air pressure and the minimum air pressure is lower than the threshold value in response to a decrease in the air pressure of at least one airbag among the airbags, the motion system is configured to switch the operating mode to the standby mode.

7. The motion pillow according to claim 6, wherein the standby mode comprises:
   a standby-maintaining step of maintaining the active mode for the predetermined first time when the second difference is lower than the threshold value;
   a re-measurement step of re-measuring air pressures of the airbags, respectively, and measuring a third difference between the maximum air pressure and the minimum air pressure among the re-measured air pressures; and
   a standby-start step of stopping supply of power to the motion pillow except for the sensor and the wireless charger only when the third difference is lower than the threshold value.

8. The motion pillow according to claim 7, wherein the motion system is further configured to maintain air injected into each of the airbags in the re-measurement step and, when a rapid increase in the air pressure of at least one airbag of the airbags occurs in the standby mode, re-switch the operating mode to the active mode to circulate air.

* * * * *